US007899555B2

(12) United States Patent
Morgan et al.

(10) Patent No.: US 7,899,555 B2
(45) Date of Patent: Mar. 1, 2011

(54) INTRAPERICARDIAL LEAD

(75) Inventors: Kevin L. Morgan, Simi Valley, CA (US); Steven R. Conger, Agua Dulce, CA (US); Anna Barlow, Santa Clarita, CA (US); Stuart Rosenberg, Canyon Country, CA (US); Wenbo Hou, Lancaster, CA (US); Michael Yang, Thousand Oaks, CA (US); Sheldon Williams, Green Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 523 days.

(21) Appl. No.: 11/691,335

(22) Filed: Mar. 26, 2007

(65) Prior Publication Data

US 2007/0239244 A1    Oct. 11, 2007

Related U.S. Application Data

(60) Provisional application No. 60/791,523, filed on Apr. 11, 2006.

(51) Int. Cl.
*A61N 1/05* (2006.01)

(52) U.S. Cl. .......................... 607/130; 607/125; 607/129

(58) Field of Classification Search ................. 607/129, 607/125, 130; 600/374; 606/41
See application file for complete search history.

(56) References Cited

U.S. PATENT DOCUMENTS

| | | | |
|---|---|---|---|
| 4,030,509 A | 6/1977 | Heilman et al. | |
| 4,154,247 A * | 5/1979 | O'Neill | 607/125 |
| 4,282,886 A * | 8/1981 | King | 607/130 |
| 4,548,203 A | 10/1985 | Tacker, Jr. et al. | |
| 4,821,723 A | 4/1989 | Baker, Jr. et al. | |
| 4,827,932 A | 5/1989 | Ideker et al. | |
| 4,971,070 A | 11/1990 | Holleman et al. | |
| 4,991,583 A | 2/1991 | Silvian | |
| 4,998,975 A | 3/1991 | Cohen et al. | |
| 5,010,894 A | 4/1991 | Edhag | |
| 5,052,407 A | 10/1991 | Hauser et al. | |
| 5,063,932 A | 11/1991 | Dahl et al. | |
| 5,105,826 A * | 4/1992 | Smits et al. | 607/119 |

(Continued)

FOREIGN PATENT DOCUMENTS

EP          0280564 B1          6/1993

(Continued)

OTHER PUBLICATIONS

European Search Report, Aug. 2, 2007: Related Application Serial No. EP07251557.

(Continued)

*Primary Examiner* — Kennedy J Schaetzle (57) ABSTRACT

The intrapericardial lead includes a lead body having a proximal portion and a flexible, pre-curved distal end portion. The distal end portion carries at least one electrode assembly containing an electrode adapted to engage pericardial tissue. The distal end portion further carries a pre-curved flexible wire member having ends attached to spaced apart points along the distal end portion of the lead body, the flexible wire member having a normally expanded state wherein an intermediate portion of the wire member is spaced apart from the distal end portion, and a generally straightened state wherein the wire member and the distal end portion are disposed in a more parallel, adjacent relationship so as to present a small frontal area to facilitate delivery into the pericardial space. The wire member re-expands to its normal state after delivery into the pericaridal space to anchor the distal end portion of the lead body relative to the pericardial tissue.

28 Claims, 10 Drawing Sheets

U.S. PATENT DOCUMENTS

| | | | | |
|---|---|---|---|---|
| 5,127,421 | A * | 7/1992 | Bush et al. | 607/130 |
| 5,170,803 | A * | 12/1992 | Hewson et al. | 607/124 |
| 5,191,901 | A | 3/1993 | Dahl et al. | |
| 5,282,845 | A * | 2/1994 | Bush et al. | 607/128 |
| 5,300,110 | A | 4/1994 | Latterell et al. | |
| 5,314,462 | A | 5/1994 | Heil, Jr. et al. | |
| 5,327,909 | A | 7/1994 | Kiser et al. | |
| 5,344,439 | A | 9/1994 | Otten | |
| 5,385,579 | A | 1/1995 | Helland | |
| 5,397,342 | A | 3/1995 | Heil, Jr. et al. | |
| 5,411,527 | A | 5/1995 | Alt et al. | |
| 5,425,756 | A | 6/1995 | Heil, Jr. et al. | |
| 5,476,503 | A | 12/1995 | Yang | |
| 5,482,037 | A * | 1/1996 | Borghi | 600/381 |
| 5,496,362 | A * | 3/1996 | KenKnight et al. | 607/129 |
| 5,509,924 | A | 4/1996 | Paspa et al. | |
| 5,562,708 | A | 10/1996 | Combs et al. | |
| 5,674,251 | A | 10/1997 | Combs et al. | |
| 5,730,127 | A * | 3/1998 | Avitall | 600/374 |
| 5,772,590 | A * | 6/1998 | Webster, Jr. | 600/374 |
| 5,837,007 | A | 11/1998 | Altman et al. | |
| 5,863,291 | A * | 1/1999 | Schaer | 606/41 |
| 5,893,847 | A * | 4/1999 | Kordis | 600/41 |
| 5,895,417 | A | 4/1999 | Pomeranz et al. | |
| 5,991,668 | A * | 11/1999 | Leinders et al. | 607/125 |
| 6,056,744 | A | 5/2000 | Edwards | |
| 6,120,496 | A | 9/2000 | Whayne et al. | |
| 6,214,002 | B1 * | 4/2001 | Fleischman et al. | 606/41 |
| 6,253,106 | B1 | 6/2001 | Legay et al. | |
| 6,330,481 | B1 | 12/2001 | Van Wijk et al. | |
| 6,463,335 | B1 | 10/2002 | Munch et al. | |
| 6,473,645 | B1 | 10/2002 | Levine | |
| 6,542,781 | B1 * | 4/2003 | Koblish et al. | 607/122 |
| 6,741,878 | B2 | 5/2004 | Fuimaono et al. | |
| 6,941,174 | B2 | 9/2005 | Shchervinsky | |
| 6,966,322 | B2 | 11/2005 | McVenes et al. | |
| 7,047,086 | B2 * | 5/2006 | Taskiran et al. | 607/126 |
| 7,158,839 | B2 * | 1/2007 | Lau | 607/129 |
| 7,200,445 | B1 | 4/2007 | Dalbec et al. | |
| 7,474,909 | B2 * | 1/2009 | Phan et al. | 600/374 |
| 2002/0151948 | A1 | 10/2002 | King | |
| 2003/0028224 | A1 | 2/2003 | McVenes et al. | |
| 2003/0195507 | A1 * | 10/2003 | Stewart et al. | 606/41 |
| 2003/0212446 | A1 | 11/2003 | Kaplan et al. | |
| 2004/0015193 | A1 | 1/2004 | Lamson et al. | |
| 2004/0054391 | A1 | 3/2004 | Wildon | |
| 2004/0059404 | A1 | 3/2004 | Bjorklund et al. | |
| 2004/0087831 | A1 | 5/2004 | Michels et al. | |
| 2004/0176782 | A1 | 9/2004 | Hanse et al. | |
| 2004/0267303 | A1 | 12/2004 | Guenst | |
| 2005/0090870 | A1 | 4/2005 | Hine et al. | |
| 2005/0102003 | A1 | 5/2005 | Grabek et al. | |
| 2005/0113900 | A1 | 5/2005 | Shiroff et al. | |
| 2005/0119718 | A1 | 6/2005 | Coe et al. | |
| 2005/0131511 | A1 | 6/2005 | Westlund | |
| 2005/0137672 | A1 | 6/2005 | Coe et al. | |
| 2005/0137674 | A1 | 6/2005 | Coe et al. | |
| 2005/0149138 | A1 | 7/2005 | Min et al. | |
| 2006/0020317 | A1 | 1/2006 | Flach et al. | |
| 2009/0299446 | A1 | 12/2009 | Jensen et al. | |

FOREIGN PATENT DOCUMENTS

| | | |
|---|---|---|
| EP | 0571985 B1 | 12/1999 |
| EP | 0589633 B1 | 1/2000 |
| WO | 02085425 A1 | 10/2002 |
| WO | 2005039691 A1 | 5/2005 |

OTHER PUBLICATIONS

NonFinal Office Action (Restriction), mailed Apr. 29, 2009: Related U.S. Appl. No. 11/760,648.

NonFinal Office Action, mailed Jun. 8, 2009: Related U.S. Appl. No. 11/760,648.

NonFinal Office Action, mailed Dec. 23, 2009 - Related U.S. Appl. No. 11/760,648.

Final Office Action, mailed Jun. 25, 2010 - Related U.S. Appl. No. 11/760,648.

* cited by examiner

INTRAPERICARDIAL LEAD

CROSS REFERENCES TO RELATED APPLICATIONS

This application claims the benefit of U.S. Provisional Application Ser. No. 60/791,523 filed Apr. 11, 2006.

FIELD OF THE INVENTION

The present invention relates generally to cardiac leads carrying electrodes for electrically stimulating body tissue and/or for sensing the electrical activity of such tissue. More particularly, the invention relates to cardiac leads configured for secure placement within the intrapericardial space of the human heart.

DESCRIPTION OF THE RELATED ART

Implantable medical devices, for example, pacemakers and cardio-defibrillators, utilize leads to form the electrical connection between a device pulse generator and the heart tissue that is to be stimulated. As is well known, the leads connecting such devices with the heart may be used for pacing or for sensing electrical signals produced by the heart or for both pacing and sensing in which case a single lead serves as a bidirectional pulse transmission link between the device and the heart. The lead typically comprises a distal end portion for carrying a tip electrode and a ring electrode. The lead may also carry one or more cardioverting and/or defibrillating shocking electrodes proximal of the ring electrode.

Various lead types for different placement approaches have been developed, including endocardial and epicardial leads. For example, an endocardial type lead is one that is inserted into a vein and guided therethrough to a target location, for example, in one or both of the chambers of the right side of the heart or within one of the veins of the coronary sinus region of the heart for left side stimulation and/or sensing. The distal end portion of an endocardial lead may carry a helical, screw-in tip element, electrically active or inactive, and/or outwardly projecting tines or nubs and/or a sinuous shape for anchoring the lead.

There are factors, however, which warrant alternatives to a transvenous lead implant approach. These factors include coronary sinus and/or coronary venous obstructions. Furthermore, the coronary veins dictate the implant location of the electrode, which can make optimal left side lead placement impossible and may cause long and unpredictable implant times. In addition, approximately 10% of the patient population is unable to receive this type of lead due to vasculature anomalies. In such cases, epicardial or myocardial type leads may be used. Such leads are attached directly to the epicardium using sutures or other fixation mechanisms such as a helical screw-in electrode that engages the myocardium. Myocardial leads typically are used for temporary pacing or for permanent pacing following open-heart surgery.

Conventional approaches to the placement of epicardial leads usually involve thoracotomies or sternotomies. Such placement techniques have disadvantages including the relatively large incisions needed to gain access to the thoracic cavity and to the heart; the difficulty of quickly and easily attaching the lead; the high rate of patient morbidity, trauma and pain; the tendency to require longer in-patient recovery times; and the unattractiveness of the scars left by the procedure.

To mitigate these disadvantages, minimally invasive lead placement techniques have been developed for placing a myocardial lead on the surface of the heart via a small, finger size opening in the chest. Such techniques may include the use of a fiber optics video camera of the type commonly used in other thoracic surgeries (for example, lung biopsies and other thoracic cavity and cardiac procedures) for visually imaging, and thereby aiding, the lead placement procedure. These minimally-invasive lead placement techniques allow for faster, safer and easier myocardial lead placements with significantly less morbidity, trauma and pain to the patient. Percutaneous access to the epicardial surface comprises an even less invasive technique, available not only to surgeons but to cardiologists as well.

U.S. Pat. No. 5,052,407, for example, discloses a lead that has an electrically active distal region with a preformed, planar, spiral configuration. Using a guide wire, the distal region of the lead can be maneuvered into the pericardial space of the heart through a small needle puncture in the pericardial sac's outer membrane or layer. Once the distal region of the lead is inside the pericardial space, the guide wire is withdrawn. As it is withdrawn, turns of the spiral form in succession within the pericardial space.

There remains a need, however, for a lead that facilitates the accurate placement and subsequent anchoring thereof within the intrapericardial space, especially for such a lead deliverable by percutaneous access.

SUMMARY OF THE INVENTION

In accordance with one specific, exemplary embodiment of the present invention, there is provided a cardiac lead comprising a lead body having a proximal portion and a flexible, pre-curved distal end portion. The distal end portion carries at least one electrode assembly containing an electrode adapted to engage pericardial tissue. The distal end portion further carries a pre-curved flexible wire member having ends attached to spaced apart points along the distal end portion of the lead body, the flexible wire member having a normally expanded state wherein an intermediate portion of the wire member is spaced apart from the distal end portion, and a generally straightened state wherein the wire member and the distal end portion are disposed in a more parallel, adjacent relationship so as to present a small frontal area to facilitate delivery into the pericardial space. The wire member re-expands to its normal state after delivery into the pericardial space to anchor the distal end portion of the lead body relative to the pericardial tissue.

Pusuant to another exemplary embodiment of the invention, there is provided a cardiac lead comprising a lead body having a proximal portion and a precurved distal end portion, the distal end portion having a distal end and a proximal end. A flexible loop member carried by the distal end portion has a proximal segment attached to the proximal end of the distal end portion and a distal segment attached to the distal end of the distal end portion, wherein the loop member has a normally expanded state in which side portions of the loop member are spaced from the precurved distal end portion. The precurved distal end portion of the lead body further carries at least one electrode coupled by an electrical conductor to an electrical contact on an electrical connector assembly attached to the proximal portion of the lead body. The pre-curved distal end portion and the loop member are adapted for percutaneous placement through the pericardial sac and into the pericardial space of a heart.

BRIEF DESCRIPTION OF THE DRAWINGS

Further objects, features and advantages of the invention will become apparent from the Detailed Description, below, when read in conjunction with the accompanying drawings in which.

DETAILED DESCRIPTION OF THE INVENTION

The present invention is directed to cardiac lead embodiments that facilitate and enhance the accurate placement (and monitoring of that placement) of medical electrodes. Although the lead embodiments may be used in a variety of medical procedures, they are especially suited for installation as a cardiac lead into the pericardial space of the heart. This installation may be made, for example, via percutaneous subxiphoid procedures. In order to best understand the novel structure of these embodiments, their placement and their subsequent use, a description of the structure is preceded by the following review of chest and heart structures.

Figure 1:
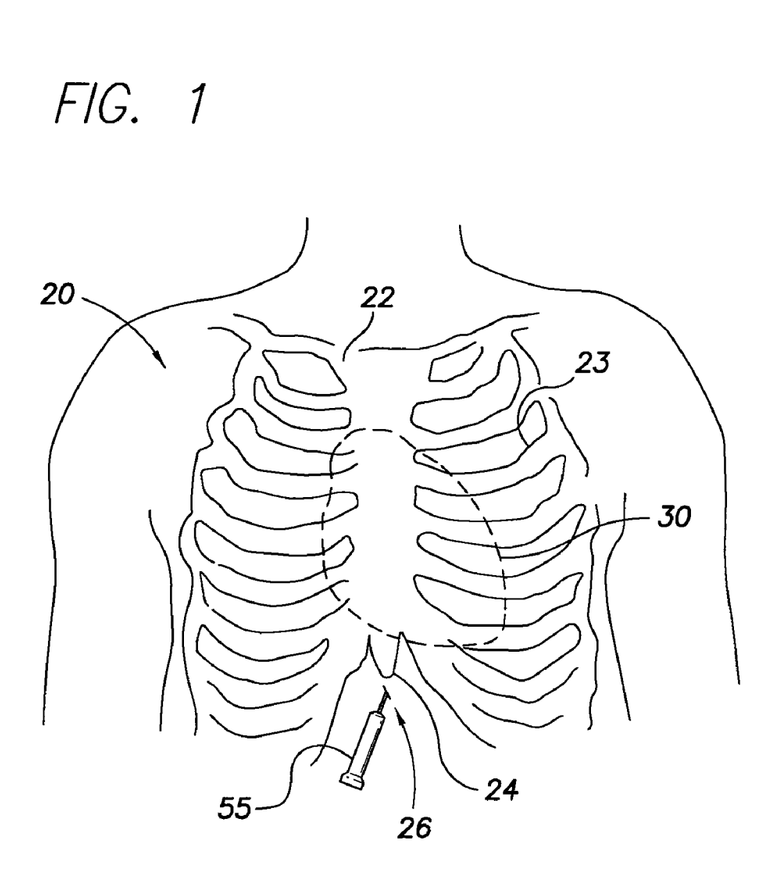
FIG. 1 is a front view of a human rib cage and the heart therein.
Figure 2:
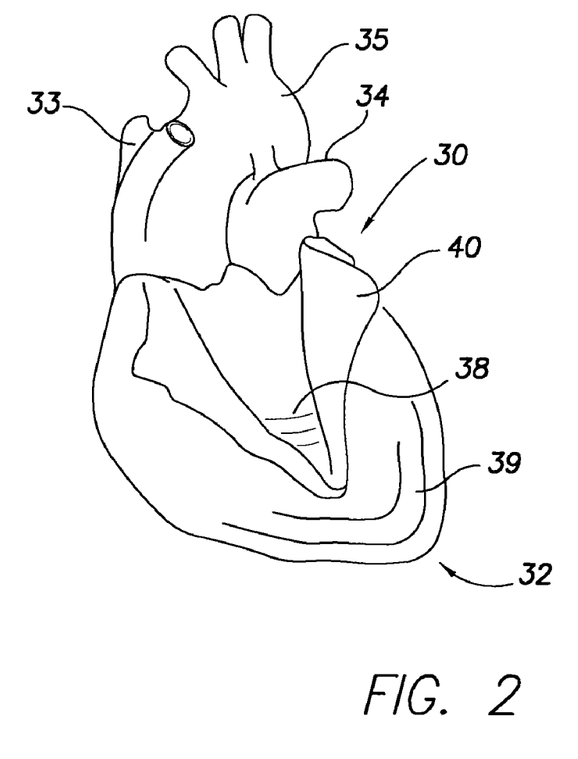
FIG. 2 is a perspective view of the heart of FIG. 1 with the pericardium partially opened to reveal the myocardium within.

FIGS. 1 and 2, respectively, illustrate these structures and, in particular, the reference numeral 20 in FIG. 1 schematically illustrates the human chest and shows the sternum 22 and the ribs 23 which attach to the sternum. The ribs and the sternum form a "rib cage" which provides a protective covering around the heart, lungs and other vital organs. Positioned at the lower end of the sternum 22, is the xiphoid process or cartilage 24. The region 26 immediately below the xiphoid process is commonly referred to as the subxiphoid region. Finally, lying within the rib cage is the heart 30 (shown in broken lines).

A perspective view of the heart 30 is shown in FIG. 2. The body of the heart extends upward from an apex 32 to where it joins with various vein and artery structures that make up the heart's blood vessels. For example, the superior vena cava 33 is one of the major vessels which passes oxygen-depleted blood from the body into the right atrium of the heart. A pair of pulmonary arteries 34 (only one shown) route blood from the right ventricle to the lungs. After oxygen-rich blood is returned from the lungs to the left atrium, the left ventricle pumps it out to the body through the aortic arch 35.

Surrounding the body of the heart 30 is the pericardium 40 which is a double walled sac of fibrous tissue that surrounds the heart up to the roots of the heart's blood vessels. In FIG. 2, the pericardium 40 has been cut and folded back to reveal the myocardium 38 which is the muscular tissue that principally forms the walls of the heart. The myocardium 38 is again shown in FIG. 3 which is an enlarged section through the heart wall. A membrane known as the endocardium 39 forms an inner lining of the myocardium and, as shown, the pericardium 40 overlies the myocardium.

Figure 3:
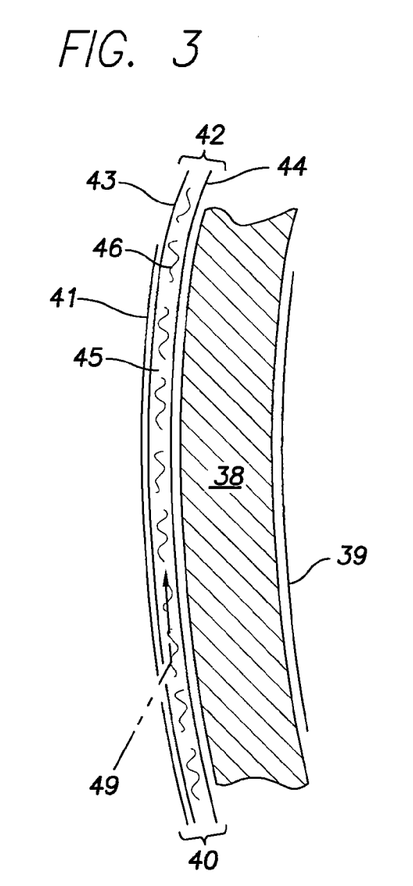
FIG. 3 is an enlarged cross section view of a portion of the wall of the heart of FIG. 2.

An outer portion of the pericardium 40 is the fibrous pericardium 41 which is formed of dense connective tissue to protect the heart and anchor it to chest structures (e.g., the diaphragm and the back of the sternum). The inner portion of the pericardium is the serous pericardium 42 which has two layers. The outer layer is the parietal pericardium 43 which lies next to the fibrous pericardium 41. The inner layer is the visceral pericardium which is typically called the epicardium 44.

The fibrous pericardium 41 and parietal pericardium 43 are collectively referred to as the "pericardial sac." The parietal 43 and visceral layers 44 are spaced apart to form the pericardial space 45 which is filled with serous fluid 46 generally called the pericardial fluid. The pericardial fluid acts to reduce surface tension and facilitate free movement of the myocardium. The term epicardial is typically used to refer to the outside surface of the heart.

Cardiac lead embodiments of the invention are configured for insertion along an insertion path 49 through the pericardial sac and into the pericardial space 45 to facilitate secure attachment to the epicardium 44. Before directing attention to the lead embodiments, a method for placing a cardiac lead of the invention will be described with reference to the flow chart 50 of FIG. 4.

Figure 4:
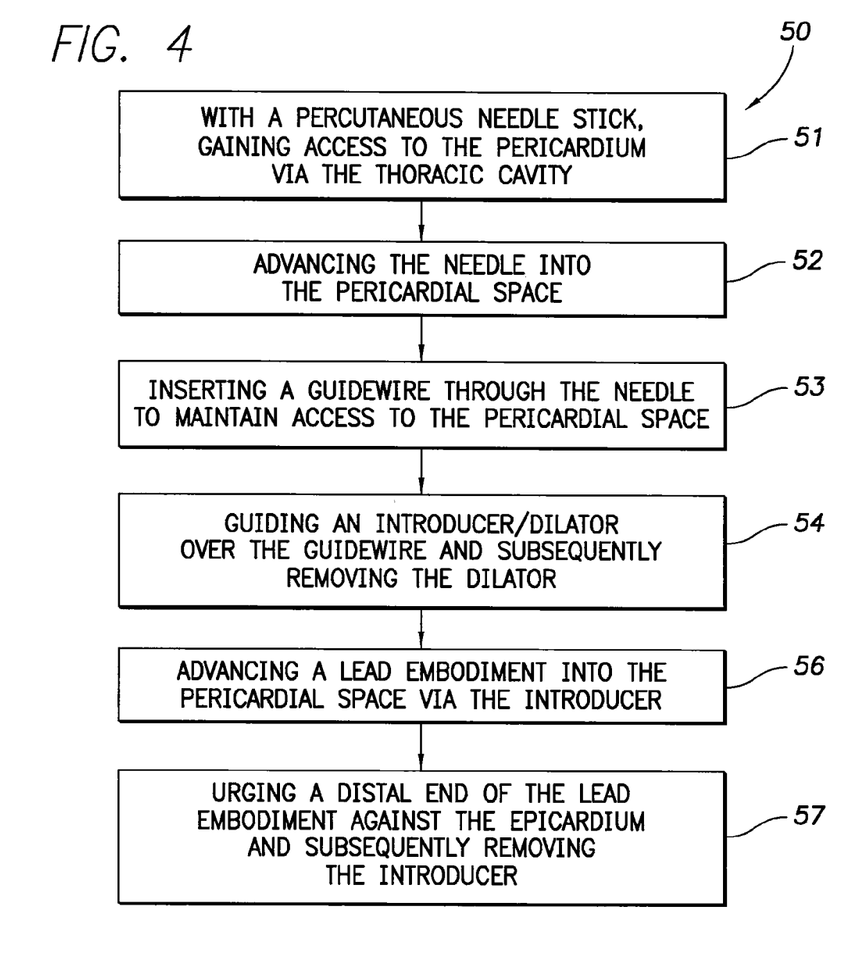
FIG. 4 is a flow chart that indicates installation processes for a cardiac lead embodiment of the present invention.

In a first step 51, a percutaneous needle stick is used to gain access to the pericardium 40 via the thoracic cavity. One embodiment of this process applies the needle stick to the subxiphoid region 26 of FIG. 1. In a second step 52, the needle is advanced along the path 49 (FIG. 3) through the pericardial sac and into the pericardial space 45. In step 53 a guidewire is inserted through the needle to maintain access to the pericardial space. In step 54 an introducer/dilator is placed over the guidewire to facilitate introduction of a cardiac lead. Subsequently, the dilator is removed leaving an introducer 55 inserted into the xiphoid region 26 as shown in FIG. 1. In step 56, the lead is advanced through the introducer 55 and into the pericardial space 45. Finally, in step 57 the distal end of the lead is urged against the epicardium 44. The introducer is then removed. Because a variety of guidewires, dilators and introducers are known in the art, their details have been omitted. One possible introducer for use in placing an intrapericardial lead is described in U.S. patent application Ser. No. 11/609, 751, titled Intrapericardial Delivery Tools and Methods, the disclosure of which is hereby incorporated by reference.

With reference now to FIGS. 5-10, there are shown specific, exemplary embodiments of intrapericardial leads in accordance with the invention. As shown in these figures, there is provided a cardiac lead 60 including a lead body 62 having a proximal portion 64 and a precurved distal end portion 66. The proximal portion 64 carries an electrical connector assembly 68 adapted to be received by a receptacle in a pacemaker or ICD 70.

Figure 7:
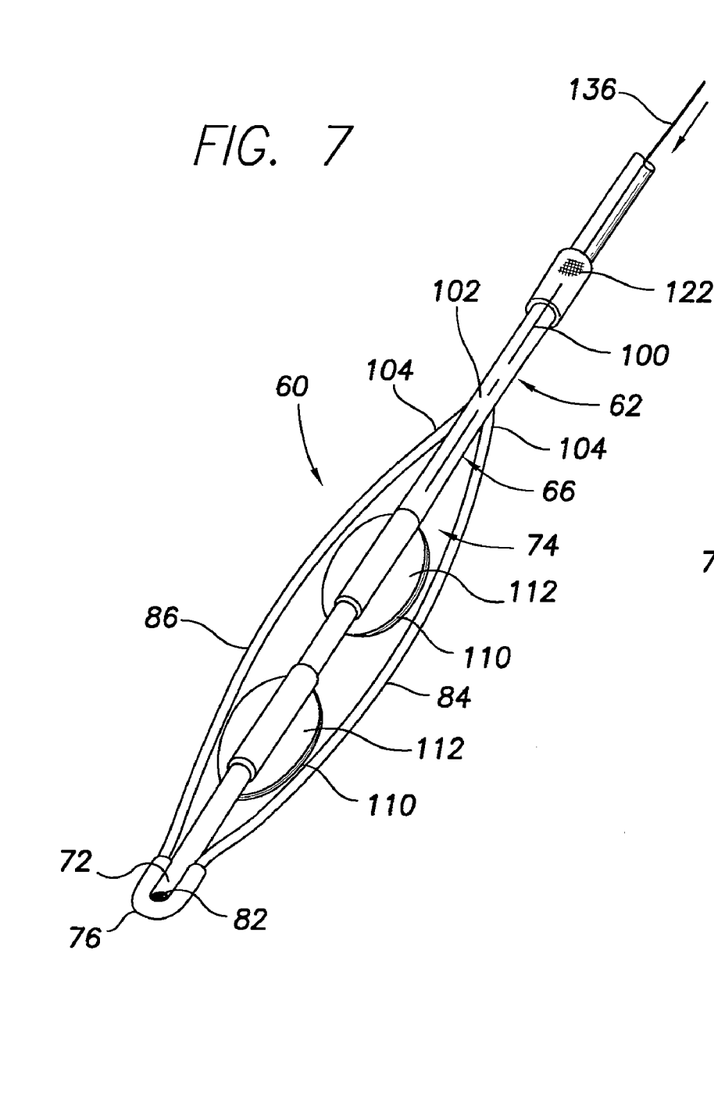
FIG. 7 is a perspective view of the lead of FIG. 5 which shows the distal end portion of the lead of FIG. 5 urged into its extended configuration suitable for passage through an introducer.

The precurved distal end portion 66 of the lead body has a preferably closed distal tip 72 and carries a precurved loop member 74 which has a distal segment 76 and is preferably formed of a flexible spring metal wire so that the loop member will recover to its relaxed loop configuration (FIGS. 5 and 8) upon being released from an extended, elongated configuration shown in FIG. 7. The closed distal tip 72 is compatible with the use of a stylet to drive the distal end portion 66 of the lead body and the loop member 74 carried thereby to a target location within the pericardial space 45. It will be apparent, however, to those skilled in the art that the distal tip 72 may have an aperture in communication with a longitudinally-extending lumen within the lead body 62 to permit delivery of the lead to its destination by means of a guide wire in accordance with well-known "over-the-wire" lead placement techniques. The lead body 62 preferably comprises a multilumen structure of silicone rubber, polyurethane or similar biocompatible, biostable material. In the example shown, the lead body 62 defines two lumens 78 (FIG. 6) for receiving electrical conductors and a third lumen 80 for receiving a stylet.

Figures 5, 6:
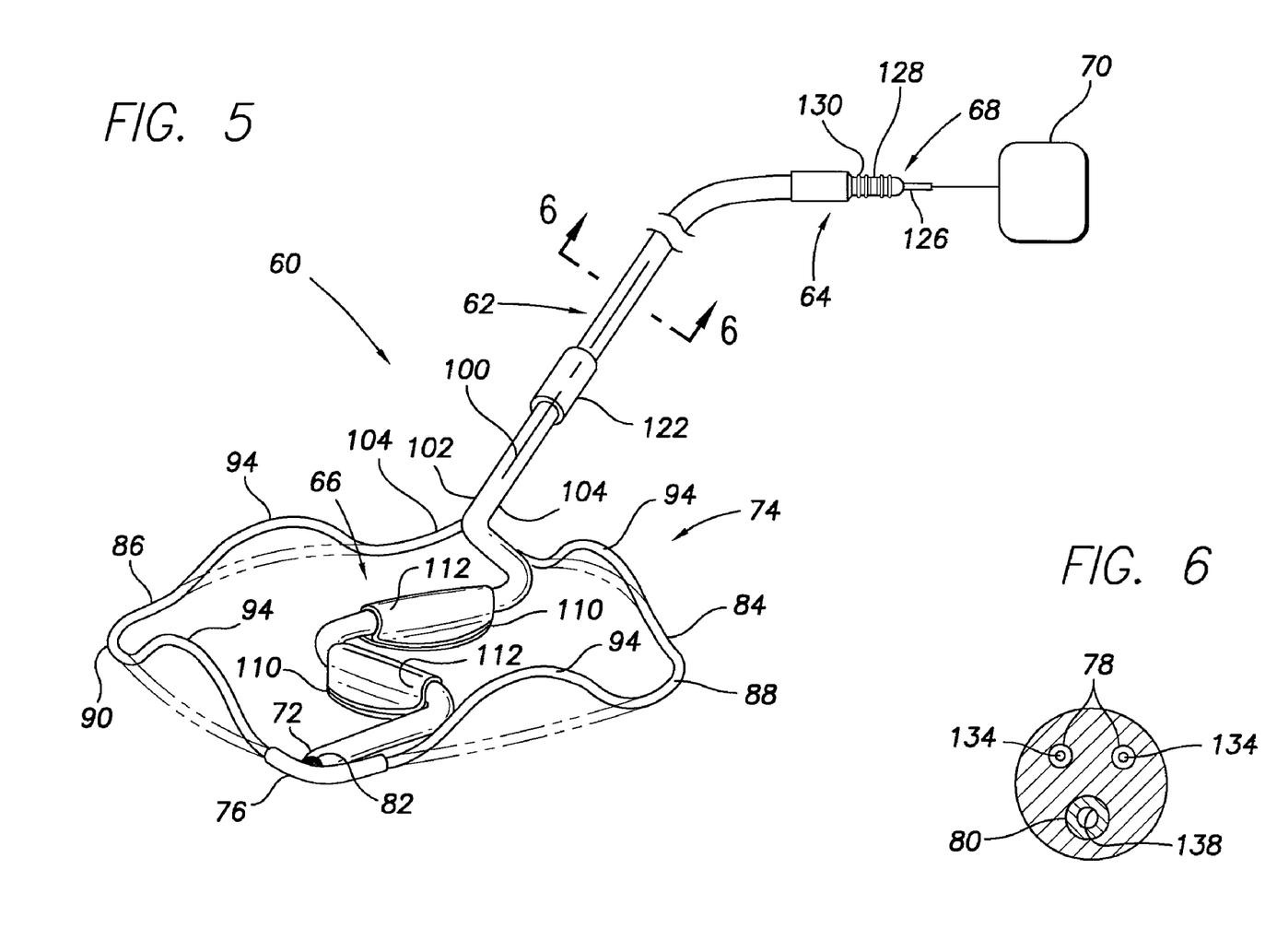
FIG. 5 is a top perspective view of a cardiac lead in accordance with one embodiment of the present invention.
FIG. 6 is a cross section view of the lead shown in FIG. 5, as seen along the line 6-6.
Figure 8:
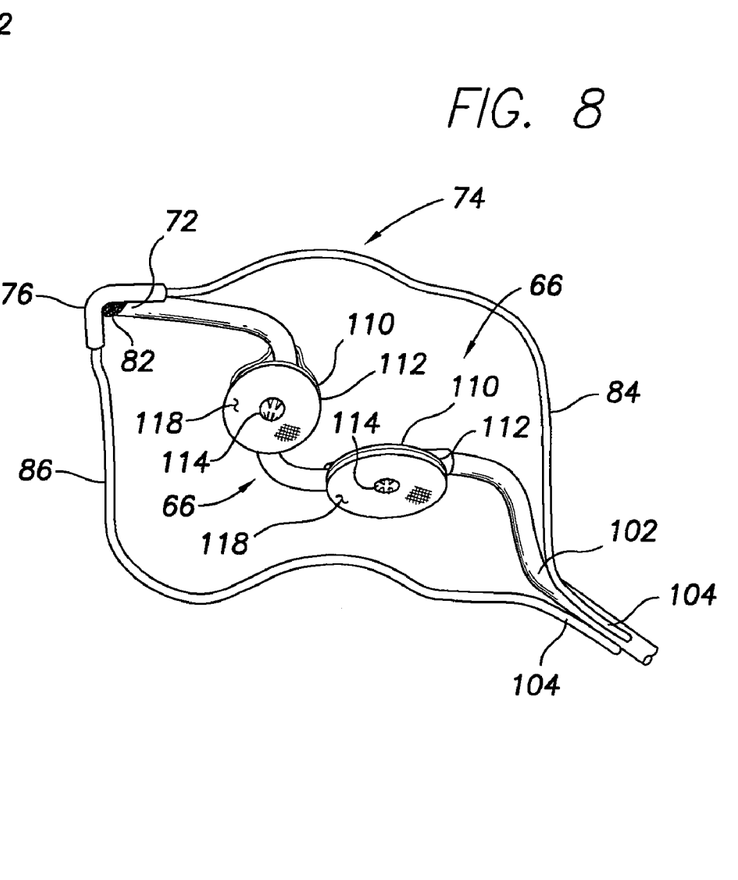
FIG. 8 is a bottom perspective view of the lead of FIG. 5.

The closed end 72 of the lead body is joined to the distal segment 76 by, for example, a medical-grade adhesive 82 and, in the example shown in FIGS. 5 and 8, the distal end portion 66 is preformed into a generally sinuous configuration.

A best seen in FIGS. 5 and 8, the wire loop member 74 comprises first and second wire wings or loop portions 84 and 86 which are positioned on opposite sides of the distal end portion 66. The loop portions 84 and 86 extend outwardly to first and second tips 88 and 90, respectively that are spaced farthest from the distal end portion 66. The inside of the wire loop member 74 defines a central region.

Figure 9:
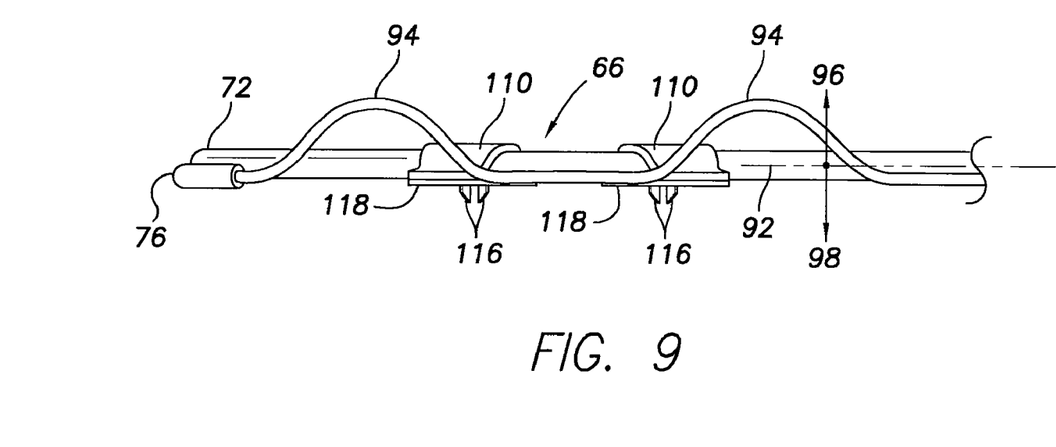
FIG. 9 is a side elevation view of the distal end portion of the lead of FIG. 5.

As is best seen in FIG. 9, the distal segment 76 and the tips 88 and 90 (not visible) substantially lie in a common plane 92 and the wire of at least one of the loop portions defines at least one undulation or hump 94. In another embodiment, each of the first and second loop portions 84 and 86 defines a pair of humps 94 that curve upwardly (as seen in FIG. 9) away from the common plane 92. FIG. 9 indicates first and second sides 96 and 98, respectively, of the common plane 92 and in the example shown, the humps 94 in the wire are shown to extend towards the first side 96.

With reference to FIG. 7, although a pair of loop portions 84 and 86 disposed symmetrically about a longitudinal center line 100 of the lead body is preferred, it will become evident from the ensuing description that other arrangements may be feasible, including, without limitation, an asymmetrical arrangement comprising a single loop portion, the provision of a pair of bilaterally disposed loop portions offset in the longitudinal direction to provide a smaller frontal area to facilitate delivery, or multiple loop portions on one or both sides of the longitudinal center line 100. In addition, in another alternative embodiment, some or all of the humps 94 may be formed to curve downwardly relative to the plane 92.

As stated above, the distal end portion 66 of the lead body 62 normally assumes a curved, sinuous configuration when it is not urged into its generally straightened configuration. The sinuous configuration extends from the distal closed end 72 to a proximal end 102 of the distal end portion and may take various curved or serpentine forms in different lead embodiments.

Similarly, the loop member 74 assumes the normally deployed or expanded state as seen in FIGS. 5 and 8. The loop member 74 extends between the distal segment 76 and bilateral proximal segments 104 which are coupled to the distal end portion 66 in the region of the proximal end 102. The loop member 74, in plan view, may take various forms. For example, the embodiment shown in FIGS. 5-10 has a generally diamond-shaped configuration. Other configurations, such as square, rectangular, circular, elliptical, and so forth, may be utilized.

The distal end portion 66 of the lead body carries at least one, and preferably a plurality of passively fixed or anchored electrode assemblies 110 within the confines of the loop member 74. Each electrode assembly 110 may comprise a shield of, for example, silicone rubber, secured to the distal end portion 66 and surrounding an electrode 114. In the lead embodiment shown, each electrode 114 carries a plurality of prongs 116 that project beyond a flat surface 118 of the corresponding shield 112. The prongs 116 serve to grip the pericardial tissue and to concentrate the electrical current density. The electrodes 114 are preferably formed from a biocompatible and biostable electrically conductive metal (e.g., gold, platinum, or titanium) or metal alloy (e.g., platinum/iridium or stainless steel). The electrode assemblies 110 are arranged along the distal end portion 66 so that the electrodes 114 and prongs 116 are directed towards the second side 98 of the common plane 92 (FIG. 9).

Figure 10:
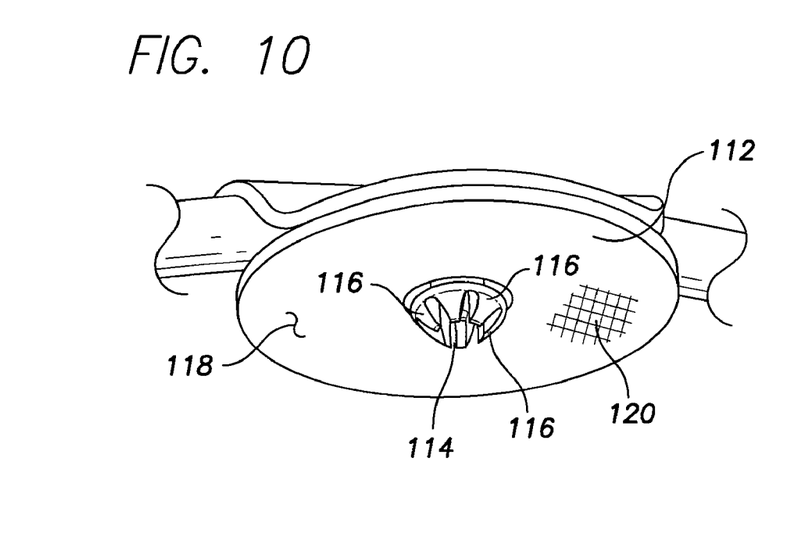
FIG. 10 is an enlarged perspective view of an electrode assembly forming part of the lead of FIG. 5.

Preferably, the surface of the shield 112 that surrounds the electrode 114 is covered with a polymer mesh 120 (FIG. 10). After the distal end portion 66 has been implanted in the pericardial space 45, fibrotic tissue grows into the mesh 120 and further fixes the electrode assemblies 110 in place. To further stabilize the lead body within the pericardial space, a mesh sleeve 122 may be provided about the lead body proximal of the distal end portion 66. After pericardial tissue has also grown into this mesh sleeve 122, the lead is further fixed within the pericardial space. To ameliorate inflammatory responses, each of the electrodes 114 may include a bore (not shown) for housing a drug dispensing member such as an absorbent drug-eluting plug loaded with a steroid solution or the like.

The electrical connector assembly 68 carried by the proximal portion 64 of the lead body comprises a pin contact 126, a ring contact 128 and annular seals 130. The connector assembly 68 is configured for insertion into a mating receptacle in the pacemaker or ICD 70.

With reference to FIG. 6, an enlarged sectional view of the lead body 62 shows electrical conductors 134 in the lumens 78 for connecting the electrodes 114 of the two electrode assemblies 110 with the pin and ring contacts 126 and 128.

The lumen 80 is configured to slidably receive a stylet 136 as shown in FIG. 7. To enhance that reception, the lumen 80 may be lined with a sleeve 138 formed of a low-friction polymer (e.g., polytetrafluoroethylene (PTFE)).

In the embodiment shown in FIGS. 5-10, the distal end portion 66 of the lead body carries two electrode assemblies 110 for bipolar pacing/sensing. In another embodiment, the distal end portion 66 of the lead body may carry more than two electrode assemblies and in yet another embodiment, the distal end portion of the lead body may carry only one electrode for unipolar pacing and/or sensing, as is well-known in the art.

The metallic loop member 74 may also facilitate application of high voltage shocks to the heart tissue in response to tachycardia or fibrillation. In an embodiment in which the device 70 is an ICD, for example, electrical shocks may be applied to the epicardium via the loop member or, alternatively, through an electrically conductive wire (not shown) wrapped about one or more of the arms of the loop member 74 and coupled to the ICD.

In an exemplary application of the cardiac lead 60 of FIGS. 5-10, the stylet 136 is inserted through the lumen 80 until it abuts the closed end 72 of the lead body. Pressure from the stylet urges the distal end portion 66 of the lead body into an extended, generally straightened, narrowed configuration and the associated loop member 74 into an extended, elongated, narrowed configuration shown in FIG. 7 to facilitate implantation via the introducer 55 (FIG. 1) in the subxiphoid region 26 and along the insertion path 49 (FIG. 3) into the pericardial space 45. In this state, the lead body 66 and the loop member 74 define a first, thin lead profile.

Figure 11:
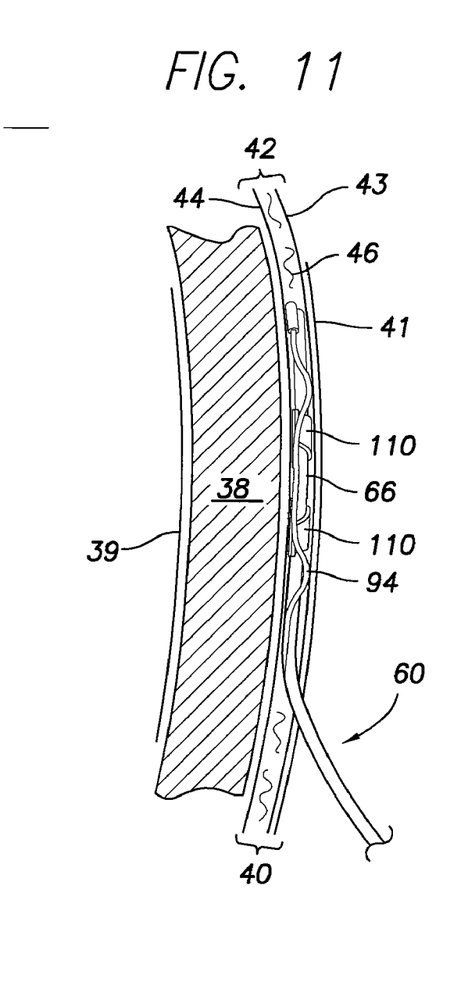
FIG. 11 is a cross section view similar to FIG. 3 showing the cardiac lead of FIG. 5 inserted into the pericardial space.

Once the distal end portion 66 of the lead body and the loop member 74 are properly placed in a desired location within the pericardial space, the stylet 136 is withdrawn permitting the distal end portion 66 and the loop member 74 to recover to their normally expanded and sinuous configurations shown in FIGS. 5 and 8. FIG. 11 is a view similar to FIG. 3 (with like elements indicated by like reference numbers) which shows the distal end portion 66 of the lead body in position in the pericardial space 45. The humps 94 of the loop member 74 abut the curved surface of the parietal layer 43 which urges the electrodes towards the epicardium 44. In this state, the lead body and the loop member 74 define a second lead profile that is wider than the first lead profile.

Essentially, the humps 94 form pressure points that urge the electrode assemblies 110 and the electrodes 114 and prongs 116 carried thereby into engagement with the epicardium. Although the humps 94 enhance this urging action, other useful embodiments of the cardiac lead 60 may be formed with planar versions of the loop member 74, that is, without humps, as shown by the broken-lines in FIG. 5. The two-dimensional profile of these planar embodiments will also be urged inward by the curved parietal layer 43.

Figure 12:
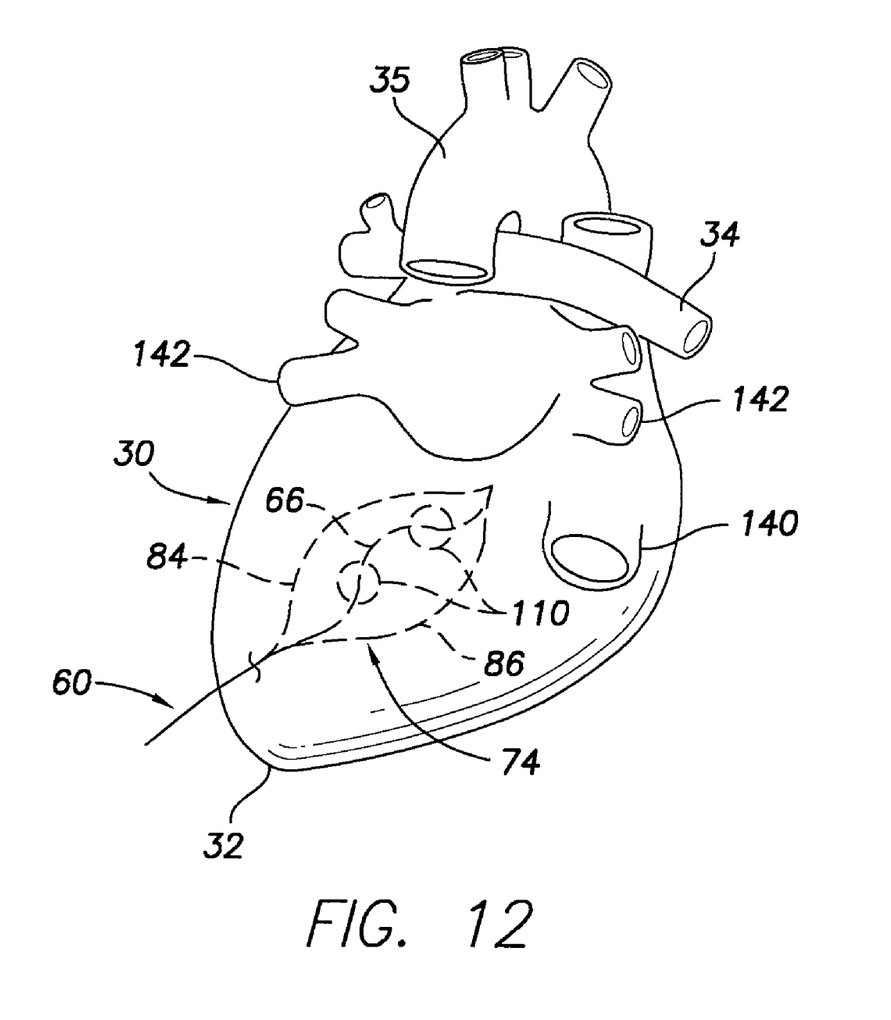
FIG. 12 is a posterior view of the heart of FIG. 2 showing the lead of FIG. 5 inserted into the pericardial space.

FIG. 12 shows a posterior view of the heart 30 with heart structures such as the inferior vena cava 140, pulmonary veins 142, pulmonary artery 34, and aortic arch 35 visible. FIG. 12 shows the lead's distal end portion 66 and the loop member 74 carried thereby inserted into the pericardial space 45 with the electrode assemblies 110 in engagement with the posterior surface overlying the left ventricle of the heart 30. Other anatomic locations may also be reached with this lead.

In a significant feature of the lead structure, the sinuous configuration of the distal end portion 66 may be used to provide verification that the lead 60 has been properly placed with the electrodes urged into engagement with the epicardium 44.

More specifically, when the lead 60 is viewed fluoroscopically, the observed sinuous configuration of the distal end portion 66 will immediately indicate the orientation of the lead and its electrodes. It can be visually confirmed, therefore, that the electrodes are directed towards the epicardium. Alternatively, if the lead 60 is viewed laterally on edge, as in FIG. 9, the offset electrode assemblies 110 will be visible and provide verification that they are directed toward the epicardium.

In another feature of the lead structure, the sinuous configuration of the distal end portion 66 provides resilience thereof between the ends 72, 102 of the distal end portion. This resilience allows the electrode assemblies 110 to move or float relative to the loop member 74 and track the movement of the epicardium as the heart beats. Contact between the electrodes 114 and the epicardium 44 is thus enhanced during heart beats. By structuring the distal end portion 66 to be less stiff than the loop member 74, the effectiveness of this feature may be further enhanced.

The loop member 74 may be formed from various resilient materials. An exemplary material is Nitinol which is a nickel-titanium alloy which has a thermal memory that will enhance its recovery to its normal, expanded configuration as it responds to body temperature. Although a medical-grade adhesive 82 may be used to join the distal segment 76 of the loop member 74 to the closed end 72 of the lead body's distal end portion, other known joinder techniques may be used, for example, reflow, insert molding, and so forth.

With reference again to FIGS. 5-10, by way of non-limiting example, the dimensions and other features of various elements of the lead may be as follows:

(1) The diameter of the lead body 62 may be 5½ French.

(2) The loop member 74, deployed as seen in FIGS. 5 and 8, may have a generally diamond configuration in plan view, measuring, for example, 6½ cm long and 4½ cm wide. It will be apparent that the loop member may have different aspect ratios (i.e., ratios of length to width). For example, an aspect ratio of approximately 1 to 1 (a generally square shape) will not have a tendency to favor one direction of heart movement over another.

(3) The overall length of the loop member 74 in its elongated, contracted configuration (FIG. 7) may be 8 cm with a contracted width of 12 French so as to be compatible with an introducer having an internal diameter of, for example, 14 French.

(4) The overall diameter of each of the electrodes 114 may be about 1.6-2.0 mm. The prongs 116 may be arranged in a generally circular array (FIGS. 8 and 10) having a diameter of about 1.9 mm.

(5) The shields 112 and meshes 120 are flexible so that they will contract as they are passed through an introducer. The shields 112 and meshes 120 may have the same diameter of approximately 1 cm; as best seen in FIG. 7, the shields and meshes are preferably somewhat elliptical in plan view with the longer axis extending longitudinally to facilitate the passage of the electrode assemblies 110 through an introducer and into the pericardial space 45.

Figure 13:
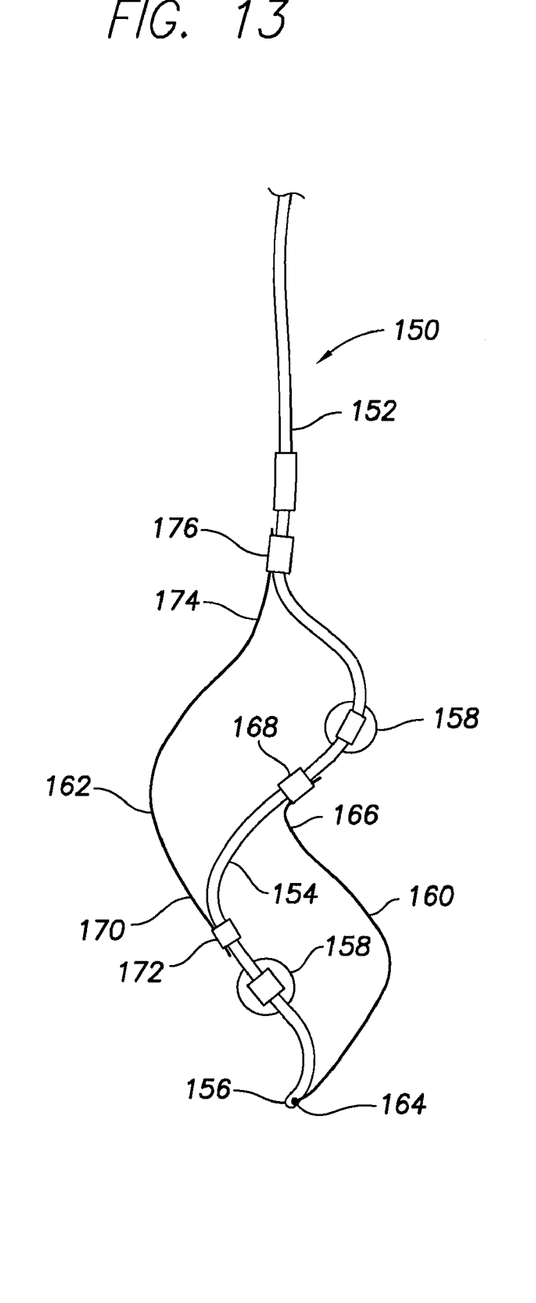
FIGS. 13 and 14 are schematic plan and side views, respectively, of an alternative embodiment of the present invention.
Figure 14:
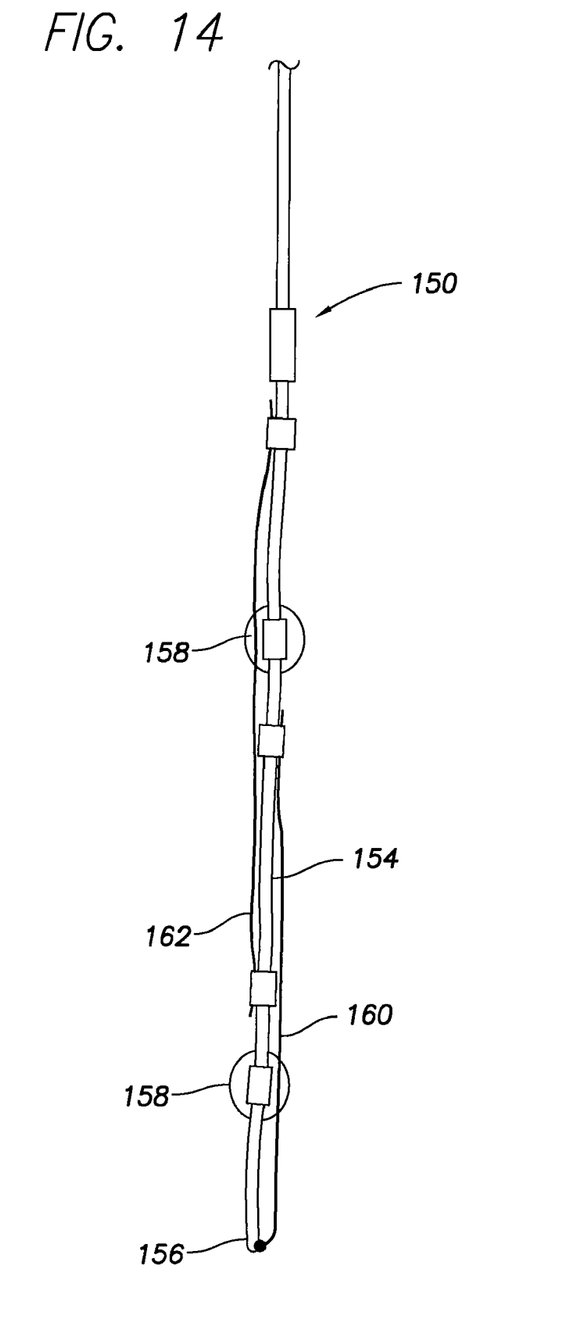

With reference to FIGS. 13 and 14, there is shown another specific exemplary embodiment of the present invention comprising a lead 150 having a lead body 152 including a pre-curved distal end portion 154 having a preferably closed distal tip 156. The distal end portion 154 carries along the length thereof at least one and preferably a plurality of electrode assemblies 158, of the type already described. In this specific example, two spaced apart electrode assemblies 158 are included. The distal end portion 154 of the lead body further carries a pair of half loop members or wings 160 and 162 that are longitudinally offset relative to each other. Thus, the distal half loop member 160 has a distal extremity 164 attached to the closed distal tip 156 of the lead body and a proximal end 166 secured at an attachment point 168 proximal of the distal tip. The proximal half loop member 162 has a distal extremity 170 attached to the distal end portion of the lead body at a point 172 intermediate the distal tip and the attachment point 168 of the first half loop member, and a proximal end 174 attached to the lead body at a point 176 proximal of the proximal attachment point 168 of the first half loop member. Accordingly, the half loop members 160 and 162 are offset relative to each other, that is, they overlap so that as shown in FIG. 14, portions of the distal end portion of the lead body present a small frontal area to facilitate passage through an associated introducer.

The half loop members 160, 162 may comprise lengths of resilient, biocompatible, biostable metal wire pre-curved to assume the configurations shown in FIG. 13. It will be evident that the half loop members 160, 162 need not have the same length. For example, the distal half loop member 160 may be shorter than the proximal loop member 162.

Figure 15:
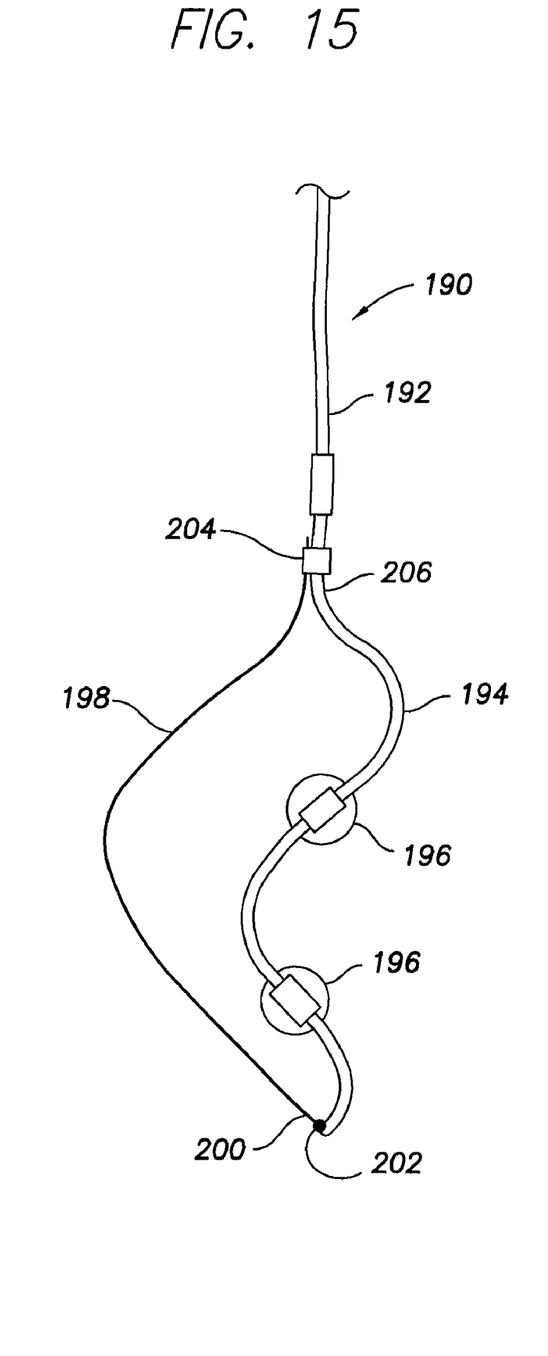
FIGS. 15 and 16 are schematic plan and side views, respectively, of another embodiment of the present invention.
Figure 16:
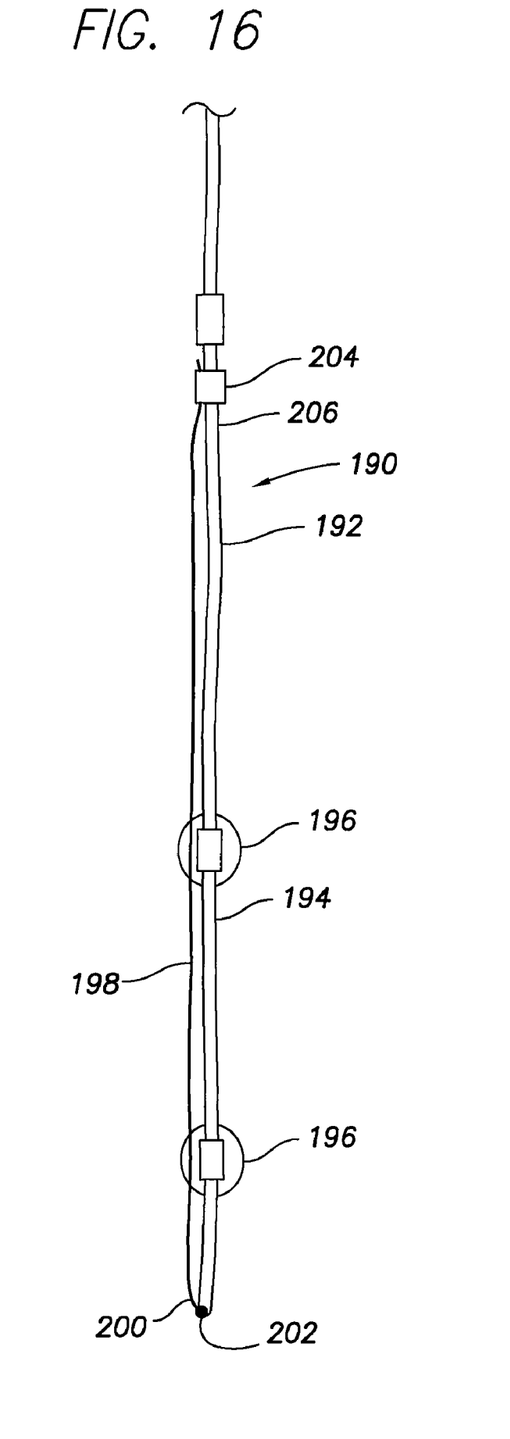

Turning to FIGS. 15 and 16, there is shown a lead 190 having a lead body 192 comprising a pre-curved distal end portion 194 along the lines already described carrying at least one and preferably a plurality of electrode assemblies 196 along with a single half loop wire member 198 extending between an attachment 200 at a closed distal tip 202 of the distal end portion 194 and an attachment 204 at a proximal end 206 of the distal end portion. As before, the half loop member or wing is preferably fabricated of a resilient, pre-curved wire member that normally assumes the deployed configuration shown in FIG. 15. An advantage of this single wing or half loop member is that the frontal area of the distal end portion may be minimized in the extended configuration of the lead body as shown in FIG. 16.

Figure 17:
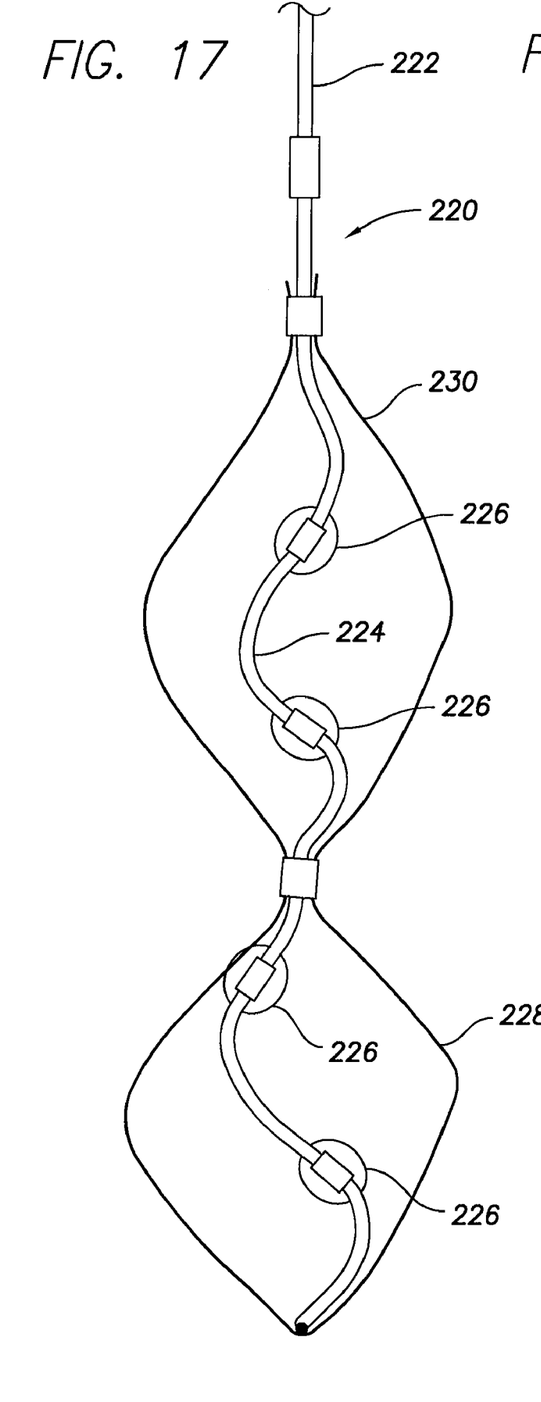
FIGS. 17 and 18 are schematic plan and side views, respectively, of yet another embodiment of the present invention.
Figure 18:
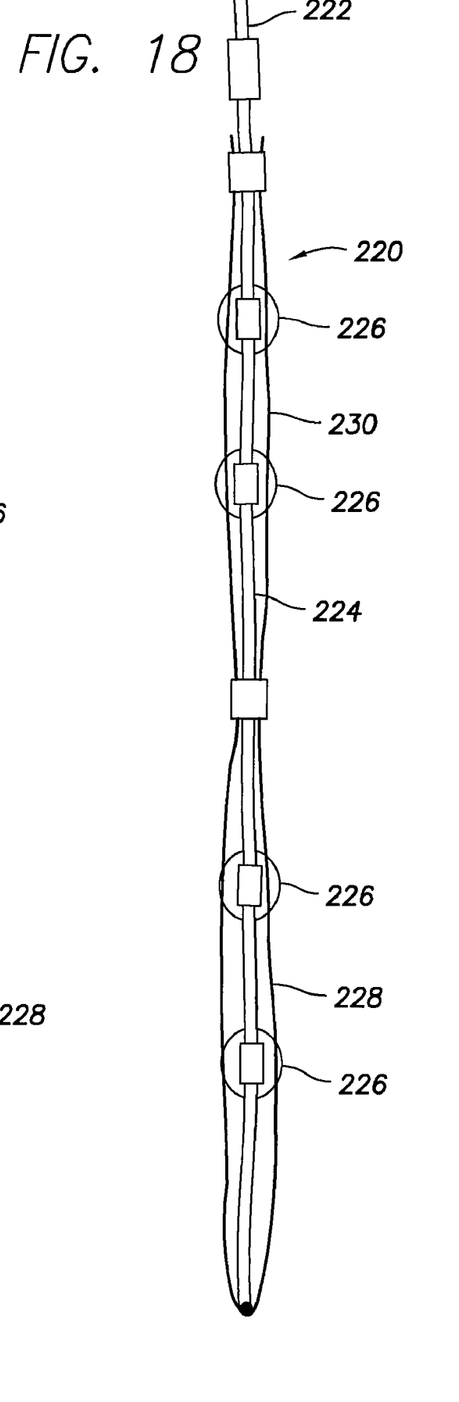
Figure 19:
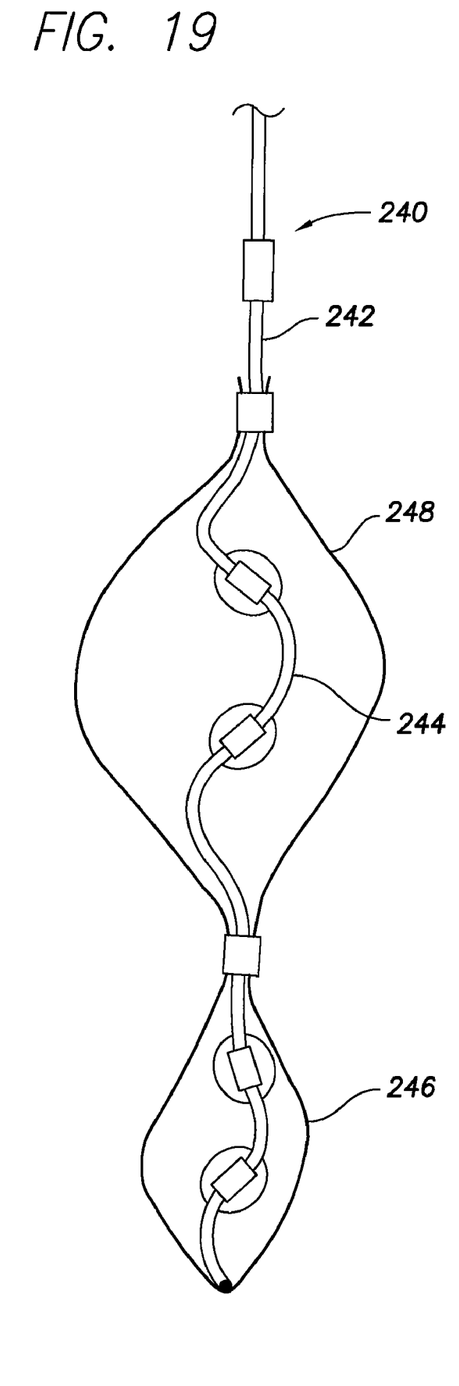
FIGS. 19 and 20 are schematic plan and side views, respectively, of still a further embodiment of the present invention.
Figure 20:
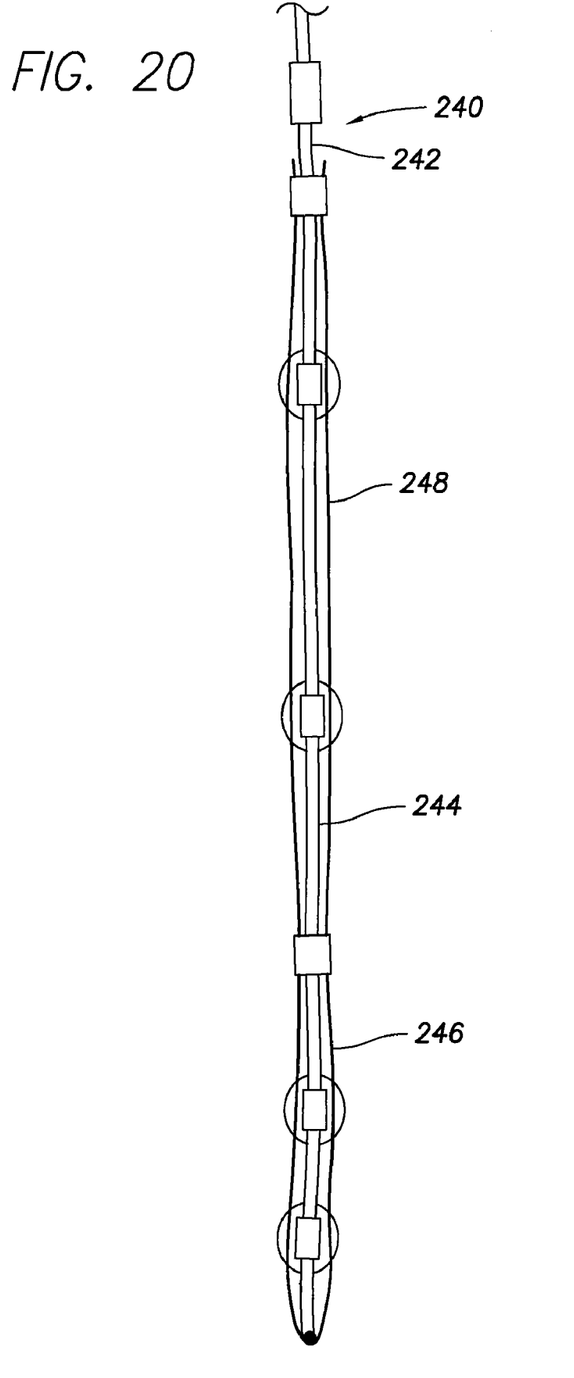

Referring to FIGS. 17 and 18, there is shown a lead 220 comprising a lead body 222 having a pre-curved distal end portion 224 carrying at least one and preferably a plurality of electrode assemblies 226 along the lines already described. The distal end portion 224 of the lead body in the embodiment of FIGS. 17 and 18 carries a pair of normally deployed or expanded wire loop members comprising a distal loop member 228 (FIG. 17) and a proximal loop member 230 attached to the distal end portion 224 proximal of the distal loop member 228. In the embodiment shown, the loop members 228 ad 230 have the same size but it will be evident that their sizes may differ. For example, in FIGS. 19 and 20, there is shown a lead 240 having a lead body 242 having a precurved distal end portion 244 carrying a pair of normally deployed or expanded wire loop members (FIG. 19) comprising a distal loop member 246 and a proximal loop member 248 wherein the distal loop member 246 is smaller than the proximal loop member 248. The smaller distal loop member 246 may be better suited for atrial placement whereas the larger proximal loop member 248 may be better sized for overlying the ventricle.

In other embodiments, the loop members carried by leads in accordance with the invention may have hemo-compatible and/or lubricious coatings, for example, an anti-inflammatory, an anti-coagulant or a coating of PTFE, or silicone rubber or polyurethane for minimizing adverse interaction with the tissue lining the pericardial sac that might lead to thrombosis.

The embodiments of the invention described herein are exemplary and numerous modifications, variations and rearrangements can be readily envisioned to achieve substantially equivalent results, all of which are intended to be embraced within the spirit and scope of the appended claims.

We claim:

1. A cardiac lead comprising:
   a lead body having a proximal portion and a precurved distal end portion having a lumen sized to receive a stylet extending there through, the distal end portion configured to assume a straightened configuration when a stylet is within the lumen, the distal end portion having a distal end and a proximal end;
   a flexible loop member carried by the distal end portion and having a proximal segment attached to the proximal end of the distal end portion and a distal segment attached to the distal end of the distal end portion, wherein the loop member has a normally expanded state in which side portions of the loop member are spaced from the precurved distal end portion, and is adapted to assume a contracted state in response to the precurved distal end portion assuming a straightened configuration;
   at least one electrode carried by the precurved distal end portion;
   an electrical connector assembly attached to the proximal portion of the lead body; and
   an electrical conductor coupling the at least one electrode with an electrical contact on the connector assembly.

2. The lead of claim 1 wherein the loop member and the precurved distal end portion generally lie in a common plane.

3. The lead of claim 2 wherein portions of the loop member are configured with undulations which extend away from the common plane.

4. The lead of claim 1 further including a second electrical conductor coupling the loop member with a second contact on the connector assembly to facilitate use of the loop as a shocking electrode.

5. The lead of claim 1 further including a medicinal coating on the loop member wherein the coating is configured to minimize adverse interaction with cardiac tissue.

6. The lead of claim 1 wherein the precurved distal end portion of the lead body has a sinuous shape.

7. The lead of claim 1 further comprising a mesh anchoring sleeve about the lead body proximal of the distal end portion thereof.

8. The lead of claim 1 wherein the flexible loop member comprises metallic, biocompatible, biostable wire.

9. The lead of claim 1 wherein the side portions of the loop member are longitudinally offset from each other along the distal end portion of the lead body.

10. The lead of claim 1 further comprising a second flexible loop member carried by the distal end portion of the lead body, the second flexible loop member being disposed proximal of the first-mentioned flexible loop member and comprising bilateral side portions spaced from the precurved distal end portion in a normally expanded state of the second flexible loop member.

11. The lead of claim 10 wherein the second flexible loop member is larger than the first-mentioned flexible loop member.

12. A lead comprising:
    a loop defining a central region and having a normally expanded state;
    a lead body having a portion positioned within the central region, wherein the portion of the lead body within the central region has a normally curved state; and
    at least one electrode on the lead body;
    the lead having an expanded state wherein the loop assumes its normally expanded state and the portion of the lead body within the central region assumes its normally curved state to define a first lead profile, and an elongated state wherein the loop assumes an elongated state and the portion of the lead body within the central region assumes a generally straightened state to define a second lead profile that is thinner than the first lead profile.

13. The lead of claim 12 wherein the loop has a width and length defining an aspect ratio of nearly 1:1 when the loop is in its normally expanded state.

14. The lead of claim 12 wherein the loop has a three-dimensional profile including at least one hump.

15. The lead of claim 12 wherein the loop has a two-dimensional profile.

16. The lead of claim 12 wherein the electrode is on the portion of the lead body within the central region of the loop.

17. The lead of claim 12 wherein the loop has a stiffness greater than the stiffness of the lead body.

18. The lead of claim 12 wherein the loop, in its normally expanded state, assumes one of a generally diamond, round or oval shape.

19. The lead of claim 12 wherein the loop is formed of a material suitable for delivering high voltage shocks.

20. The lead of claim 12 wherein the lead body comprises a lumen configured to receive a stylet and the lead body is configured to assume its generally straightened state upon receiving a stylet.

21. A cardiac lead comprising:

a lead body having a proximal portion and a flexible, pre-curved distal end portion configured to be straightened, the distal end portion carrying at least one electrode assembly containing an electrode adapted to engage pericardial tissue, the distal end portion further carrying a pre-curved flexible wire member having ends attached to spaced apart points along the distal end portion of the lead body, the flexible wire member having a normally expanded state wherein an intermediate portion of the wire member is spaced apart from the distal end portion, and a generally straightened state wherein the wire member and the distal end portion are disposed in a more parallel, adjacent relationship so as to present a small frontal area to facilitate delivery into the pericardial space, the wire member re-expanding to its normal state after delivery into the pericardial space to anchor the distal end portion of the lead body relative to the pericardial tissue, wherein straightening of the precurved distal end portion causes the wire member to contract to its generally straightened state; wherein the distal end portion of the lead body carries a second pre-curved flexible wire member having ends attached to spaced apart points along the distal end portion of the lead body, the second flexible wire member having a normally expanded state wherein an intermediate portion of the second flexible wire member is spaced apart from the distal end portion of the lead body, and a generally straightened state wherein the second flexible wire member and the distal end portion are disposed in a more parallel, adjacent relationship so as to present a small frontal area to facilitate delivery into the pericardial space, the second flexible wire member re-expanding to its normal state after delivery into the pericardial space to anchor the distal end portion of the lead body relative to the pericardial tissue;

the first and second flexible wire members are offset relative to each other along the distal end portion of the lead body; and the first and second flexible wire members have distal and proximal ends and the wire members are offset relative to each other such that both the distal ends and the proximal ends of the respective wire members are offset from each other.

22. The lead of claim 21 wherein:
the flexible wire member includes at least one undulation for enhancing the anchoring of the distal end portion of the lead body.

23. The lead of claim 21 wherein:
the first and second flexible wire members together define in their normally expanded states a generally loop shaped member.

24. The lead of claim 23 wherein:
the at least one electrode assembly is disposed within the confines of the generally loop-shaped member.

25. The lead of claim 21 wherein:
the at least one electrode assembly comprises a flexible shield surrounding the electrode.

26. The lead of claim 25 wherein:
the shield carries a mesh element for inducing tissue ingrowth to aid in anchoring the electrode assembly relative to the pericardial tissue.

27. The lead of claim 21 wherein:
the electrode carries projecting prongs for engaging the pericardial tissue to stabilize the portion of the electrode relative to the tissue.

28. The lead of claim 21 wherein the flexible, pre-curved distal end portion is configured to receive a stylet and to be straightened thereby.

* * * * *